United States Patent
Naringrekar et al.

(10) Patent No.: US 8,632,805 B2
(45) Date of Patent: *Jan. 21, 2014

(54) CONTROLLED-RELEASE FORMULATIONS, METHOD OF MANUFACTURE, AND USE THEREOF

(75) Inventors: Gandha V. Naringrekar, Princeton, NJ (US); Kristin A. Arnold, Morrisville, PA (US); David Erkoboni, Pennington, NJ (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 506 days.

This patent is subject to a terminal disclaimer.

(21) Appl. No.: 12/143,460

(22) Filed: Jun. 20, 2008

(65) Prior Publication Data

US 2009/0317473 A1    Dec. 24, 2009

(51) Int. Cl.
*A61K 9/22* (2006.01)
(52) U.S. Cl.
USPC .......... 424/468; 424/451; 424/464; 424/465; 424/469; 424/484; 424/488; 424/489
(58) Field of Classification Search
None
See application file for complete search history.

(56) References Cited

U.S. PATENT DOCUMENTS

| | | | |
|---|---|---|---|
| 5,837,379 A | 11/1998 | Chen et al. | |
| 6,331,316 B1 * | 12/2001 | Ullah et al. | 424/482 |
| 6,350,786 B1 | 2/2002 | Albano et al. | |
| 7,794,750 B2 * | 9/2010 | Naringrekar et al. | 424/468 |
| 2003/0219489 A1 | 11/2003 | Curatolo et al. | |
| 2004/0118007 A1 | 6/2004 | Chickering, III et al. | |
| 2004/0234602 A1 | 11/2004 | Fischer et al. | |
| 2004/0253310 A1 | 12/2004 | Fischer et al. | |
| 2005/0019399 A1 | 1/2005 | Fischer et al. | |
| 2006/0287352 A1 | 12/2006 | Holm et al. | |
| 2007/0026082 A1 | 2/2007 | Lizio et al. | |
| 2007/0185147 A1 | 8/2007 | Fleischer et al. | |

FOREIGN PATENT DOCUMENTS

EP    0210540 A1    2/1987

OTHER PUBLICATIONS

Kranz, H. et al., "Development of a single unit extended release formulation for ZK 811 752, a weakly basic drug" European Journal of Pharmaceutical Sciences, vol. 26, pp. 47-53 (2005).

* cited by examiner

*Primary Examiner* — Hasan Ahmed
(74) *Attorney, Agent, or Firm* — Cooley LLP

(57) ABSTRACT

The present invention includes a controlled-release composition having a matrix. The matrix contains a pharmaceutically effective amount of an active agent or a pharmaceutically acceptable salt, solvate, ester, and/or prodrug thereof, an ionic non-gelling matrix polymer, and a pH modifier. The ionic non-gelling matrix polymer is practically insoluble and unswellable at a first aqueous fluid pH and is soluble at a second aqueous fluid pH. The pH modifier is present in an amount to control the release of the active agent from the composition. The controlled-release composition is substantially free of a gelling or swellable excipient. The present invention also provides methods of making and using the controlled-release compositions.

31 Claims, No Drawings

CONTROLLED-RELEASE FORMULATIONS, METHOD OF MANUFACTURE, AND USE THEREOF

FIELD OF THE INVENTION

The present invention generally relates to a controlled-release composition as well as a method of preparing and using the composition.

BACKGROUND OF THE INVENTION

For a drug to achieve its therapeutic effect, it needs to reach the target site in the body and further maintain the required level of blood or plasma concentration. Due to the short half-life of the active ingredient, many drugs need to be administered multiple times a day to maintain the desirable blood or plasma concentration. Furthermore, even with multiple administrations of such a drug per day, the blood or plasma concentrations of the active ingredient may still vary with time, i.e., at certain time points between administrations there are higher concentrations of the active ingredient than at other times. Thus, at certain time points of a 24-hour period, a patient may receive therapeutically effective amounts of the active ingredient, while at other time points the concentration of the active ingredient in the blood may fall below therapeutic levels. Additional problems with such drugs include that multiple dosing a day often adversely affects patient compliance with the treatment. Therefore, it is desirable to have a drug dosage form wherein the active ingredient is delivered in such a controlled manner that a constant or substantially constant level of blood or plasma concentration of the active ingredient can be achieved for 24 hours by one or at most two dosing. Accordingly, the present invention provides a controlled-release composition as described below.

SUMMARY OF THE INVENTION

In one embodiment, the present invention provides a controlled-release composition, which comprises a matrix containing a pharmaceutically effective amount of an active agent or a pharmaceutically acceptable salt, solvate, ester, and/or prodrug thereof, an ionic non-gelling matrix polymer that is practically insoluble and unswellable at a first aqueous fluid pH and is soluble at a second aqueous fluid pH, and a pH modifier present in an amount to control the release of the active agent from the composition. The controlled-release composition is substantially free of a gelling or swelling excipient.

In another embodiment, the present invention provides a method of preparing a controlled-release composition. The method comprises blending a pharmaceutically effective amount of an active agent or a pharmaceutically acceptable salt, solvate, ester, and/or prodrug thereof, an ionic non-gelling matrix polymer that is practically insoluble and unswellable at a first aqueous fluid pH and is soluble at a second aqueous fluid pH, and a pH modifier present in an amount to control the release of the active agent from the composition to form a matrix mixture; compressing the matrix mixture to form a tablet or mini-tablet, or pelletizing the matrix mixture to form pellets, or filling the matrix mixture into a gelatin capsule.

These and other embodiments, advantages and features of the present invention become clear when detailed description and examples are provided in subsequent sections.

DETAILED DESCRIPTION OF THE INVENTION

The present invention includes a controlled-release composition comprising a matrix. The matrix comprises a pharmaceutically effective amount of an active agent or a pharmaceutically acceptable salt, solvate, ester, and/or prodrug thereof, an ionic non-gelling matrix polymer, and a pH modifier. The controlled release composition is substantially free of a gelling or swelling excipient. The ionic non-gelling matrix polymer is practically insoluble and unswellable at a first aqueous fluid pH and is soluble at a second aqueous fluid pH. The pH modifier is present in an amount to control the release of the active agent from the composition.

By "ionic non-gelling matrix polymer", it is meant an ionic polymer that only swells slightly or does not swell to form a gel when exposed to an aqueous medium. The ionic non-gelling matrix polymer typically has a pH-dependent solubility. That is, it is practically insoluble and unswellable at a first aqueous fluid pH, and soluble at a second aqueous fluid pH. The term "soluble" denotes between 10 and 30 mL of solvent required to dissolve 1 gram of solute, as defined in the United States Pharmacopeia, 2003 (the "USP"). The term "practically insoluble" or "insoluble" denotes 10,000 mL or more of solvent required to dissolve 1 gram of solute, as defined in the USP.

According to one embodiment, the first aqueous fluid pH can be equal to or less than about 4.5. Preferably, the first aqueous fluid pH is from about 1.0 to about 4.5. More preferably, the first aqueous fluid pH is from about 1.0 to about 4.0. Even more preferably, the first aqueous fluid pH is from about 1.0 to about 3.5. The second aqueous fluid pH can be greater than about 4.5. Preferably, the second aqueous fluid pH is from about 4.6 to about 7.5. More preferably, the second aqueous fluid pH is from about 5.0 to about 7.5. An exemplary first aqueous fluid can be human gastric fluid, and an exemplary second aqueous fluid can be human intestinal fluid.

Exemplary ionic non-gelling matrix polymers include cellulose acetate phthalate (e.g., powder: pH 6.2, available from Eastman Chemical Co. as C-A-P; Dispersion: pH: 6.0, available from FMC BioPolymer as AquaCoat® CPD), cellulose acetate succinate (e.g., LF: pH 5.5; MF: pH 6.0; HF: pH 6.8; LG; pH 5.5; MG: pH 6.0; HG: 6.8, F grades are an aqueous dispersion and G grades are from solvent available from Shin-Etsu under the trade name AQOAT®), hypromellose phthalate (HPMCP) (e.g., Grade HP-50: pH 5.0; Grade HP-55: pH 5.5 available from Shin-Etsu), hypromellose acetate succinate (HPMCAS), polyvinylacetate phthalate (e.g., aqueous dispersion: pH 5.0; Powder: pH 5.0 available from Colorcon, the aqueous dispersion under the trade name Sureteric® and the powder under the trade name Opadry® Enteric), hydroxyethyl cellulose phthalate, cellulose acetate maleate, cellulose acetate trimellitate, cellulose acetate butyrate, cellulose acetate propionate, methacrylic acid-methyl methacylate co-polymers (e.g., Type A: pH 6.0; Type B: pH 7.0 both available from Degussa/Evonik with the trade names EUDRAGIT® L 100 for Type A and EUDRAGIT® S 100 for Type B), methacrylic acid-ethylacrylate co-polymers (available under the trade name EUDRAGIT® L, e.g., L100-55), methacrylic acid-methyl acrylate-methyl methacrylate co-polymers (available under the trade name EUDRAGIT® FS-30D for delivery above pH 7.0), and the like or combinations comprising at least one of the foregoing. Methacrylic acid-methyl methacylate co-polymers, methacrylic acid-ethylacrylate co-polymers, and/or methacrylic acid-methyl acrylate-methyl methacrylate co-polymers are also known as polymethacrylates as described in the Handbook of Pharmaceutical Excipients, 2006, the Fifth Edition, edited by Raymond C Rowe, Paul J. Sheskey, and Sian C Owen, pages 553 to 560, the content of which is incorporated by references in its entirety. EUDRAGIT® is a trademark of Evonik Industries. The specifications for various EUDRAGIT® products including the above-mentioned ones can be found in the manufacture's product manual or on the website for the corresponding EUDRAGIT® product, the content of which is incorporated by references in its entirety.

The ionic non-gelling matrix polymer can be present in an amount from about 5 to about 85 wt %, specifically from about 20 to about 50 wt %, more specifically from about 30 to about 40 wt % of the total weight of the controlled-release composition.

Not wishing to be bound by theory, it is believed the non-gelling matrix systems are less susceptible to the effects of food as compared to gelling matrix systems, such as hydroxypropyl methylcellulose. Food can affect dissolution and absorption of a tablet matrix in a number of ways including changes in pH, emulsifiers/surface tension, gastric retention, attrition, lipids, and transport. Gelling matrices are composed of high molecular weight polymers which are swellable in aqueous fluid via hydration. Upon administration, these high molecular weight polymers swell to form a gel creating a barrier to slow down the release of the active agent bound in the gel matrices. The polymers in the gel matrices hydrate slowly and require reasonable quantities of fluid to form a gel layer for diffusion. Food intake may substantially reduce the amount of free water for gel hydration. Water is particularly depleted in the lower gastrointestinal tract resulting in the possibility of unhydrated matrix being eliminated together with the active agent bound therein.

The gelling matrices have non-pH dependent solubility, i.e., having low solubility in both highly acidic pH or less acidic to basic pH. A highly acidic pH may be found in the stomach and a less acidic to basic pH may be found in the intestine. By "highly acidic pH", it is meant a pH from about 1 to about 4. By "less acidic to basic pH", it is meant a pH of greater than about 4 to about 7.5, specifically about 6 to about 7.5. Thus, even when water is sufficient, the gelling matrices may still result in inefficient and incomplete delivery of the active agent bound therein because gelling matrices can dissolve incompletely in the gastrointestinal tract. This incomplete dissolution is usually aggravated after food intake. Consequently, elimination of a portion of an undissolved gelling matrix results in the elimination of the active agent bound therein.

An ionic non-gelling matrix polymer practically insoluble in an acidic media allows for the active agent bound therein to be released from the composition through diffusion and possibly a small amount of erosion in the stomach or the upper part of the gastrointestinal tract. As the composition travels along the gastrointestinal tract, the pH increases and thereby allows for the matrix to dissolve and continue to release the active agent in a controlled or sustained manner. As the composition travels further in the gastrointestinal tract where the pH further increases, the ionic non-gelling matrix polymer will be solubilized thereby releasing the remaining active agent. Such a mechanism allows for the efficient and possibly more complete release of the active agent and limits the amount of active agent trapped in the composition. Furthermore, the complete dissolution of the ionic non-gelling matrix polymer is delayed until after it is exposed to the pH at which the ionic non-gelling matrix polymer is soluble. Such a delayed dissolution enables delivery of some amount of the active agent significantly after the time when the dose is administered. This mechanism aids in achieving blood levels sufficient to result in a once a day composition.

In the present invention, the release of the active agent from the controlled-release composition is extended for longer than it would be in an immediate-release dosage form, e.g., at least over several hours. The present controlled-release composition can provide, for example, sustained-release, delayed-release, or pulsed-release of the active agent at a particular time. The present controlled-release composition can provide for an increased duration of the active agent action, permitting for example, once-daily or twice-daily dosing.

By "immediate-release" or "instant-release", it is meant a conventional or non-modified release in which greater than or equal to about 75% of the active agent is released within two hours of administration, specifically within one hour of administration.

By "controlled-release", it is meant a dosage form in which the release of the active agent is controlled or modified over a period of time. Controlled can mean, for example, extended-, sustained-, delayed-, timed-, or pulsed-release at a particular time. Alternatively, controlled can mean that the release of the active agent is extended for longer than it would be in an immediate-release dosage form, e.g., at least over several hours.

Furthermore, the controlled-release composition is substantially free of a gelling or swelling excipient. The term "excipient" denotes any inert or slightly active substance which is used in preparing the composition as a vehicle or medium of administration for the active agent. By "gelling or swelling excipient", it is meant an excipient that swells to form a gel when exposed to an aqueous medium. The gelling or swelling polymer is typically non-pH dependent. That is, the aqueous solubility of the gelling or swelling polymer at various pH is the same or substantially the same. The gelling or swelling excipient includes a gelling or swelling polymer, such as, for example, hydroxypropyl methyl cellulose (HPMC), gums, and the like. HPMC, also known as hypromellose as described in the Handbook of Pharmaceutical Excipients, 2006, the Fifth Edition, edited by Raymond C Rowe, Paul J. Sheskey, and Sian C Owen, pages 345 to 349, the content of which is incorporated by references in its entirety.

By "substantially free", it is meant the controlled-release composition contains no or very small amount of gelling or swelling excipient. In one embodiment, the controlled-release composition contains less than 5 wt % of a gelling or swelling excipient. In another embodiment, the controlled-release composition contains less than 3 wt % of a gelling or swelling excipient. In yet another embodiment, the controlled-release composition contains less than 1 wt % of a gelling or swelling excipient.

An "active agent" means a compound, macromolecule, element, substance, or mixture that when administered to a patient, alone or in combination with another compound, macromolecule, element, substance, or mixture, confers, directly or indirectly, a physiological effect on the patient. The indirect physiological effect may occur via a metabolite or other indirect mechanism. When the active agent is a compound, then salts, solvates (including hydrates), esters, and prodrugs of the compound are contemplated herein. Furthermore, crystalline forms, non-crystalline forms, and any polymorphs of the compound are also contemplated herein. The compounds may contain one or more asymmetric elements, such as stereogenic centers, stereogenic axes, and the like, e.g., asymmetric carbon atoms, so that the compounds can exist in different stereoisomeric forms. These compounds can be, for example, racemates or in optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example, a chiral HPLC column. All forms are contemplated herein regardless of the methods used to obtain them.

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Salts" include derivatives of an active agent, wherein the active agent is modified by making acid or base addition salts thereof. Examples of pharmaceutically acceptable salts include, but are not limited to, mineral or organic acid addition salts of basic residues such as amines; alkali or organic addition salts of acidic residues; and the like, or a combination comprising one or more of the foregoing salts. The pharmaceutically acceptable salts include salts and the quaternary ammonium salts of the active agent. For example, acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, or a combination comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; or a combination comprising one or more of the foregoing salts.

By "pharmaceutically effective amount", it is meant the amount of an active agent that, when administered to a patient for treating a disease, is sufficient to effect such treatment for the disease. The "pharmaceutically effective amount" will vary depending on the active agent, the disease and its severity, and the age, weight, and other conditions of the patient to be treated.

"Solvate" means a complex formed by solvation (the combination of solvent molecules with molecules or ions of the active agent of the present invention), or an aggregate that consists of a solute ion or molecule (the active agent of the present invention) with one or more solvent molecules. In the present invention, the preferred solvate is hydrate.

"Prodrug" refers to a precursor of the active agent wherein the precursor itself may or may not be pharmaceutically active but, upon administration, will be converted, either metabolically or otherwise, into the active agent or drug of interest. For example, prodrug includes an ester or an ether form of an active agent.

In one embodiment, the active agent is selected from those having a solubility of greater than or equal to about 2.0 mg/ml in an aqueous medium at room temperature. "Room temperature" includes a temperature from about 20 to about 25° C. The aqueous medium includes water or a water solution having a pH of about 7. One example of the active agent is quetiapine or quetiapine fumarate. Quetiapine fumarate has an aqueous solubility of 3.29 mg/ml at 25° C., specifically at a pH of about 7. The solubility of an active agent can easily be determined by one having ordinary skill in the art without undue experimentation.

Various active agents or combinations thereof can be used in the controlled-release compositions described herein. Exemplary active agents include, but are not limited to: antihypertensives including ACE inhibitors, antidepressants, antianxiety agents, anticlotting agents, anticonvulsants, blood glucose-lowering agents, decongestants, antihistamines, antitussives, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, antiviral agents, anti-neoplastics, barbituates, sedatives, nutritional agents, beta blockers, emetics, anti-emetics, diuretics, anticoagulants, cardiotonics, androgens, corticoids, anabolic agents, growth hormone secretagogues, anti-infective agents, coronary vasodilators, carbonic anhydrase inhibitors, antiprotozoals, gastrointestinal agents, serotonin antagonists, anesthetics, hypoglycemic agents, dopaminergic agents, anti-Alzheimer's Disease agents, anti-ulcer agents, platelet inhibitors, glycogen phosphorylase inhibitors, muscle relaxants, and combinations thereof.

Exemplary antihypertensives include prazosin, nifedipine, trimazosin, amlodipine, and doxazosin mesylate.

Exemplary antidepressants include citalopram, escitalopram, fluoxetine, paroxetine, sertraline, amitriptyline, desipramine, imipramine, nortriptyline, venlafaxine, duloxetine, bupropion, trazodone, nefazodone, maprotiline, mirtazpine, isocarboxazid, phenelzine, and tranlcypromine.

Exemplary antianxiety agents include hydroxyzine hydrochloride, lorazepam, buspirone hydrochloride, pazepam, chlordiazepoxide, meprobamate, oxazepam, trifluoperazine hydrochloride, clorazepate dipotassium, and diazepam.

Exemplary anticlotting agents include clopidogrel.

Exemplary anticonvulsants include phenobarbital, phenytoin, primidone, carbamazepine, valproate, felbamate, gabapentin, lamotrigine, topiramate, tiagabine, diazepam; vigabatrin, oxcarbazepine, zonisamide, and levetiracetam.

Exemplary blood glucose-lowering agents include biguanides, sulfonylureas, meglitinides, thiazolidinediones, dipetidyl-peptidase-4 inhibitors, and alpha glucosidase inhibitors.

Exemplary decongestants include pseudoephedrine and phenylephrine.

Exemplary antitussives include antimony pentasulfide, benproperine, benzonatate, bibenzonium bromide, butamirate, carbocisteine, clobutinol, clofedanol, cloperastine, codeine, corex, delsym, dextromethorphan, dextropropoxyphene, dibunate, dimemorfan, dimethoxanate, domiodol, dropropizine, droxypropine, erdosteine, fedrilate, letosteine, levodropropizine, levopropoxyphene, levoverbenone, meprotixol, morclofone, neltenexine, nepinalone, normethadone, noscapine, novrad, oxeladin, oxolamine, oxtriphylline, pentoxyverine, phensidyl, pholcodine, piperidione, prenoxdiazine, tipepidine, and zipeprol.

Exemplary anti-inflammatory agents include non-steroidal anti-inflammatory drugs such as alicylates, arylalkanoic acids, profens, fenamic acids, pyrazolidine derivatives, oxicams, COX-2 Inhibitors, and sulphonanilides.

Exemplary antipsychotic agents include typical antipsychotic agents such as chlorpromazine, fluphenazine, haloperidol, molindone, thiothixene, thioridazine, trifluoperazine, loxapine, perphenazine, prochlorperazine, pimozide, thiothixene, zuclopenthixol; and atypical antipsychotic agents such as aripiprazole, clozapine, olanzapine, olanzapine/fluoxetine, risperidone, quetiapine, and ziprasidone.

Exemplary cognitive enhancers include donepezil, galantamine, memantine, and rivastigmine.

Exemplary cholesterol-reducing agents include statins such as atorvastatin, cerivastatin, fluvastatin, lovastatin, mevastatin, pitavastatin, pravastatin, rosuvastatin, and simvastatin.

Exemplary antiobesity agents include phendimetrazine, phentermine, diethylpropion, benzphetamine, mazindol, sibutramine, and orlistat.

Exemplary autoimmune disorder agents include remicade, enbrel and humira.

Exemplary anti-impotence agents include sildenafil citrate, vardenafil, and tadalafil.

Exemplary antibiotics include aminoglycosides, ansamycins, cephalosporins, glycopeptides, macrolides, and penicillins; and antifungal include econazole, terconazole, fluconazole, voriconazole, and griseofulvin.

Exemplary hypnotics/anesthetics include alfaxalone, etomidate, chlordiazepoxide and triazolam.

Exemplary antivirals include acyclovir, nelfinavir, and virazole.

Exemplary anti-neoplastics include chlorambucil, lomustine, echinomycin, tubulazole, thiabendazole and oxfendazole.

Exemplary vitamins/nutritional agents include retinol and vitamin E.

Exemplary emetics include apomorphine.

Exemplary diuretics include chlorthalidone and spironolactone.

Exemplary anticoagulants include dicumarol.

Exemplary cardiotonics include digoxin and digitoxin.

Exemplary androgens include 17-methyltestosterone and testosterone.

Exemplary corticoids include desoxycorticosterone.

Exemplary antihistamines include astemizole, levocabastine, cetirizine, and cinnarizine.

Exemplary gastrointestinal agents include loperamide and cisapride.

Exemplary serotonin antagonists include ketanserinand mianserin.

Exemplary anesthetics include lidocaine.

Exemplary anti-emetics include dimenhydrinate.

Exemplary dopaminergic agents include L-DOPA.

Exemplary anti-Alzheimer agents include zcetylcholinesterase inhibitors such as donepezil, galantamine, and rivastigmine; and NMDA antagonists such as memantine.

Exemplary anti-ulcer agent/H2 antagonists include famotidine.

Exemplary vasodilators include alprostadil.

Exemplary platelet inhibitors include prostacyclin.

Exemplary ACE inhibitors/antihypertensives include enalaprilic acid and lisinopril.

Exemplary muscle relaxants include metaxalone.

The pH modifier can be any excipient added to the controlled-release matrix to control the pH of the matrix internal environment. In one embodiment, the pH modifier can maintain the pH of the matrix internal environment such that the matrix remains in a pH range where the ionic non-gelling matrix polymer is insoluble. Thus, the integrity of the matrix can be maintained longer than when the pH modifier is not used. In one embodiment, as the pH modifier is eventually dissolved from the matrix by the gastrointestinal fluids, the pH of the matrix will experience the pH of the immediate surrounding environment. If the surrounding environment is at a pH where the ionic non-gelling matrix polymer is soluble, the polymer will dissolve thus allowing release of the active agent contained therein.

The pH modifiers suitable for the present invention include, but are not limited to pharmaceutically acceptable acids, bases, and buffer systems. Exemplary pH modifiers include organic acids or their salts, such as, alkali metal salts and alkaline earth metal salts prepared from the organic acids. Suitable organic acids include acetic acid, trifluoroacetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, mesylic acid, esylic acid, besylic acid, sulfanilic acid, 2-acetoxybenzoic acid, fumaric acid, toluenesulfonic acid, methanesulfonic acid, ethane disulfonic acid, oxalic acid, isethionic acid, an acid having a formula of $HOOC-(CH_2)n-COOH$ wherein n is 1 to 4, and the like; or a combination comprising one or more of the foregoing acids or their salts. Exemplary pH modifiers include sodium citrate, citric acid, and the like.

The pH modifier is present in the matrix in an amount that extends the release of the active agent from the controlled-release composition substantially longer than from a similar controlled-release composition free of the pH modifier. Exemplary amounts include about 2.0 to about 50 wt %, specifically about 5.0 to about 20 wt %, and more specifically about 10 to about 15 wt % based on the total weight of the controlled-release composition.

The controlled-release matrix may further optionally comprise an additional pharmaceutically acceptable excipient, lubricant, or glidant. The additional pharmaceutically acceptable excipient, lubricant, or glidant can be any of those known in the pharmaceutical art. Exemplary excipients include microcrystalline cellulose or powdered cellulose, which can act as compression aids; low molecular weight methyl cellulose (e.g., having a number average molecular weight from about 1000 to about 30,000), ethylcellulose, low molecular weight hydroxypropyl cellulose (e.g., having a number average molecular weight from about 1000 to about 50,000), low molecular weight hydroxypropyl methylcellulose (e.g., having a number average molecular weight from about 9000 to about 30,000 and a viscosity from about 1 to about 50 mPa s for a 2% (w/v) aqueous solution at 20° C.), polyvinyl alcohol, polyvinyl acetate, dicalcium phosphate, titanium dioxide, talc, alumina, starch, kaolin, polacrilin potassium, low molecular weight polyvinyl pyrrolidone (e.g., having a number average molecular weight from about 1000 to about 30,000), hydroxyethyl cellulose, sugar polyols, monosaccharides, disaccharides, polysaccharides, or a combination comprising at least one of the foregoing additional excipients.

In one embodiment, the additional pharmaceutically acceptable excipient is a soluble, non-gelling pharmaceutically acceptable excipient. The soluble, non-gelling pharmaceutically acceptable excipient can act as a pore former allowing for the formation of channels in the matrix thereby increasing the rate of active agent diffusion from the matrix at the first aqueous fluid pH. Use of the soluble, non-gelling pharmaceutically acceptable excipient provides for another means to modify the release of the active agent from the composition at a targeted rate.

In one embodiment, the soluble, non-gelling pharmaceutically acceptable excipient comprises a pharmaceutically acceptable sugar polyol, monosaccharide, or disaccharide.

Exemplary soluble non-gelling pharmaceutically acceptable excipients include, but are not limited to lactose, sucrose, dextrose, fructose, glucose, maltose, polydexotrose, sorbitol, xylitol, mannitol, galactitol, maltitol, lactitol, erythritol, maltose, dextrin, maltodextrin, xylose, galactose, trehalose, tagatose, and a combination comprising at least one of the foregoing.

The soluble, non-gelling pharmaceutically acceptable excipient can be present in the matrix in an amount from about 1 to about 70 wt %, specifically about 5 to about 50 wt %, and more specifically about 10 to about 30 wt % based on the total weight of the controlled-release composition.

The lubricant can be any substance capable of reducing friction by making surfaces smooth or slippery. Examples of suitable lubricants include solid fatty acids (for example fatty acids having from about 16 to about 22 carbon atoms), the alkaline earth metal salts thereof, particularly the magnesium and calcium salts, stearic acid, magnesium stearate, sodium stearyl fumarate, stearic acid, zinc stearate, glyceryl behenate, talc, mineral oil (in PEG), vegetable oil, hydrogenated vegetable oil, or a combination comprising one or more of the foregoing lubricants.

The lubricant can be present in the matrix in an amount of up to about 10 wt %, specifically about 0.5 to about 8 wt %, more specifically about 1.0 to about 5.0 wt %, and yet more specifically about 1.5 wt % to about 3.0 wt % of the total weight of the controlled-release composition.

The glidant can be any substance that enhances the flow of a granular mixture by reducing interparticle friction and that is used in the pharmaceutical production of tablets, capsules, pellets, etc. Examples of suitable glidants include silicon dioxide (AEROSIL, Degussa), fumed or colloidal silica. The glidant can be present in the matrix in amounts of up to about 10 wt %, specifically about 0.25 to about 5 wt %, and more specifically about 0.5 to about 1wt % of the total weight of the controlled-release composition.

The controlled-release compositions can be prepared into solid dosage forms or oral dosage form. Exemplary solid dosage forms include tablets, capsules, pellets, compressed powders, mini-tablets, and granules. By "oral dosage form", it is meant to include a unit dosage form for oral administration such as tablets, capsules (including compressed powder fill into capsules, mini-tablets to be filled into capsules, and pellets to be filled into capsules), suspensions, liquids, emulsions, and the like. An oral dosage form may optionally comprise a plurality of subunits such as, for example, microcapsules or microtablets. Multiple subunits may be packaged for administration in a single dose.

By "subunit", it is meant to include a composition, mixture, particle, pellet, etc., that can provide an oral dosage form alone or when combined with other subunits.

Dosage forms can be combination dosage forms having both immediate-release and controlled-release characteristics, such as, for example, a combination of immediate-release pellets and controlled-release pellets. The immediate-release portion of a combination dosage form may be referred to as a loading dose.

The present controlled-release compositions can be prepared by various conventional mixing, comminution and fabrication techniques readily apparent to those skilled in the art of drug formulations. Examples of such techniques include, but are not limited to: (1) Direct compression using appropriate punches and dies, where the punches and dies are fitted to a suitable rotary tableting press; (2) Injection or compression molding using suitable molds fitted to a compression unit; (3) Granulation followed by compression; and (4) Extrusion in the form of a paste into a mold or to an extrudate to be cut into lengths.

Processes such as direct compression, wet granulation in a high shear mixer, fluid bed granulation, roller compaction, extrusion/spheronization, and fluid bed pellet layering can be employed in manufacturing a solid dosage form. The granulations can be further processed by compression into tablets, mini-tablets or compressed and filled into capsules. Pellets produced from extrusion/spheronization or fluid bed layering can be filled into capsules. Techniques and compositions for making tablets (compressed and molded), capsules (hard and soft gelatin) are also described in Remington's Pharmaceutical Sciences, 1553-1593 (1980).

When compressed tablets, mini tablets or compact filled capsules are used, in particular if the matrix is directly compressed, the addition of lubricants and glidants may be helpful and sometimes important to promote powder flow and to prevent capping of the particle (breaking off of a portion of the particle) when the pressure is relieved. Useful lubricants and glidants as well as the amounts that can be used are described above.

The controlled-release compositions can optionally be further coated. The coating can be any suitable coating, such as, a functional, multi-functional, and/or non-functional coating. By "functional coating", it is meant to include a coating that modifies the release properties of the total formulation, for example, a sustained-release coating. By "non-functional coating", it is meant to include a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

The coating material may include a polymer, such as a film-forming polymer, for example, methyl cellulose, ethyl cellulose, hydroxypropyl cellulose, hydroxypropyl methyl cellulose, hydroxybutyl methyl cellulose, cellulose acetate, cellulose propionate, cellulose acetate propionate, cellulose acetate butyrate, cellulose acetate phthalate, carboxymethyl cellulose, cellulose triacetate, cellulose sulphate sodium salt, poly(methyl methacrylate), poly (ethyl methacrylate), poly (butyl methacrylate), poly (isobutyl methacrylate), poly (hexyl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, (poly propylene), poly (ethylene glycol poly (ethylene oxide), poly (ethylene terephthalate), poly(vinyl alcohol), poly(vinyl isobutyl ether), poly(vinyl acetate), poly (vinyl chloride), polyvinyl pyrrolidone, or a combination comprising one or more of the foregoing polymers. The coating material can be commercially available coatings, such as, for example the Opadry® coating system from Colorcon. The coating may comprise about 0 wt % to about 40 wt % of the composition.

The coating material can comprise optional components, such as, for example, pharmaceutically acceptable plasticizers, colorants, dyes, pigments, surfactants, flavorants, or combinations comprising at least one of the foregoing.

Known methods can be used to apply the coating to the controlled-release composition. Processes such as simple or complex coacervation, interfacial polymerization, liquid drying, thermal and ionic gelation, spray drying, spray chilling, fluidized bed coating, pan coating, electrostatic deposition, may be used. A substantially continuous nature of the coating may be achieved, for example, by spray drying from a suspension. By "substantially continuous coating", it is meant a coating which retains a smooth and continuous appearance when magnified 1000 times under a scanning electron microscope and wherein no holes or breakage of the coating are evident.

For active agents that are intended to be absorbed into the bloodstream, bioavailability data for a given formulation may provide an estimate of the relative fraction of the administered dose that is absorbed into the systemic circulation. "Bioavailability" means the extent or rate at which an active agent is absorbed into a living system or is made available at the site of physiological activity.

"Bioavailability" can be characterized by one or more pharmacokinetic parameters. Release forms may also be characterized by their pharmacokinetic parameters. "Pharmacokinetic parameters" describe the in vivo characteristics of an active agent (or surrogate marker for the active agent) over time, such as plasma concentration (C), $C_{max}$, $C_n$, $C_{24}$, $T_{max}$, and AUC. "$C_{max}$" is the measured concentration of the active agent in the plasma at the point of maximum concentration. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. The $AUC_{0-\infty}$ or $AUC_{0-INF}$ is the calculated area under the curve of plasma concentration versus time from time 0 to time infinity.

In some embodiments, the controlled-release composition is bioequivalent to a Reference drug. "Reference drug" means an active pharmaceutical ingredient product as described in the U.S. Federal Food and Drug Administration's (FDA) Orange Book, Approved Drug Products with Therapeutic Equivalence Evaluations.

"Bioequivalence" means the absence of a significant difference in the rate and extent to which the active agent or surrogate marker for the active agent in pharmaceutical equivalents or pharmaceutical alternatives becomes available at the site of action when administered in an appropriately designed study.

In one embodiment, bioequivalence is any definition thereof as promulgated by the U.S. Food and Drug Administration or any successor agency thereof. In a specific embodiment, bioequivalence is determined according to the Federal Drug Administration's guidelines and criteria, including "GUIDANCE FOR INDUSTRY BIOAVAILABILITY AND BIOEQUVALENCE STUDIES FOR ORALLY ADMINISTERED DRUG PRODUCTS—GENERAL CONSIDERATIONS" available from the U.S. Department of Health and Human Services (DHHS), Food and Drug Administration (FDA), Center for Drug Evaluation and Research (CDER) March 2003 Revision 1; and "GUIDANCE FOR INDUSTRY STATISTICAL APPROACHES TO ESTABLISHING BIOEQUIVALENCE" DHHS, FDA, CDER, January 2001, both of which are incorporated herein in their entirety.

In another embodiment, bioequivalence is determined according to the European Medicines Agency (EMEA) document "Note for Guidance on the Investigation of Bioavailability and Bioequivalence", issued Jul. 26, 2001, available from EMEA.

In one embodiment, the reference drug is a "quetiapine reference drug", i.e., a quetiapine furmarate extended release product as described in U.S. Federal Food and Drug Administration's New Drug Application No. 022047 approved on May 17, 2007 as provided in the U.S. Federal Food and Drug Administration's Orange Book, Approved Drug Products with Therapeutic Equivalence Evaluations. SEROQUEL XR is a quetiapine fumarate extended release tablet product at strengths of 50 mg, 200 mg, 300 mg, and 400 mg base equivalent which is marketed by AstraZeneca. SEROQUEL XR, 400 mg base equivalent strength is the "reference listed drug" under 21 CFR 314.94(a)(3)), i.e., the listed drug identified by FDA as the drug product upon which an applicant relies in seeking approval of an ANDA.

In one embodiment, the present invention provides a quetiapine controlled-release composition comprising a matrix containing quetiapine fumarate, an ionic non-gelling matrix polymer that is practically insoluble and unswellable at a first aqueous fluid pH and is soluble at a second fluid pH, and a pH modifier present in an amount to control the release of quetiapine fumarate from the composition, wherein the composition exhibits a ratio of a geometric mean of logarithmic transformed $AUC_{0-\infty}$ of the composition to a geometric mean of logarithmic transformed $AUC_{0-\infty}$ of quetiapine reference drug from about 0.80 to about 1.25.

In another embodiment, the present invention provides a quetiapine controlled-release composition comprising a matrix containing quetiapine fumarate, an ionic non-gelling matrix polymer that is practically insoluble and unswellable at a first aqueous fluid pH and is soluble at a second fluid pH, and a pH modifier present in an amount to control the release of quetiapine fumarate from the composition, wherein the composition exhibits a ratio of a geometric mean of logarithmic transformed $AUC_{0-t}$ of the composition to a geometric mean of logarithmic transformed $AUC_{0-t}$ of quetiapine reference drug from about 0.80 to about 1.25.

In yet another embodiment, the present invention provides a quetiapine controlled-release composition comprising a matrix containing quetiapine fumarate, an ionic non-gelling matrix polymer that is practically insoluble and unswellable at a first aqueous fluid pH and is soluble at a second fluid pH, and a pH modifier present in an amount to control the release of quetiapine fumarate from the composition, wherein the composition exhibits a ratio of a geometric mean of logarithmic transformed $C_{max}$ of the composition to a geometric mean of logarithmic transformed $C_{max}$ of quetiapine reference drug from about 0.70 to about 1.43.

In yet another embodiment, the present invention provides a quetiapine controlled-release composition comprising a matrix containing quetiapine fumarate, an ionic non-gelling matrix polymer that is practically insoluble and unswellable at a first aqueous fluid pH and is soluble at a second fluid pH, and a pH modifier present in an amount to control the release of quetiapine fumarate from the composition, wherein the composition exhibits a ratio of a geometric mean of logarithmic transformed $C_{max}$ of the composition to a geometric mean of logarithmic transformed $C_{max}$ of quetiapine reference drug from about 0.80 to about 1.25.

In one embodiment, a quetiapine controlled-release composition is bioequivalent to the tablet formulations commercially available in the United States, for example the reference drug of New Drug Application No. 022047.

In an embodiment, bioequivalence of a quetiapine controlled-release composition to a reference drug is determined by an in vivo pharmacokinetic study to determine a pharmacokinetic parameter for the quetiapine controlled-release composition. Specifically, bioequivalence can be determined by an in vivo pharmacokinetic study comparing a pharmacokinetic parameter for the two compositions. A pharmacokinetic parameter for the quetiapine controlled-release composition or the reference drug can be measured in a single or multiple dose bioequivalence study using a replicate or a nonreplicate design. For example, the pharmacokinetic parameters for quetiapine controlled-release composition of the present invention and for a reference drug can be measured in a single dose pharmacokinetic study using a two-period, two-sequence crossover design. Alternately, a four-period, replicate design crossover study may also be used. Single doses of the test composition and reference drug are administered and blood or plasma levels of the active agent are measured over time. Pharmacokinetic parameters characterizing rate and extent of active agent absorption are evaluated statistically.

The area under the plasma concentration-time curve from time zero to the time of measurement of the last quantifiable concentration ($AUC_{0-\infty}$) and to infinity ($AUC_{0-\infty}$), $C_{max}$, and $T_{max}$ can be determined according to standard techniques. Statistical analysis of pharmacokinetic data is performed on logarithmic transformed data (e.g., $AUC_{0-t}$, $AUC_{0-\infty}$, or $C_{max}$ data) using analysis of variance (ANOVA).

Under U.S. FDA guidelines, two products (e.g. an inventive composition and brand drug) or methods (e.g., dosing under non-fasted versus fasted conditions) are bioequivalent if the 90% Confidence Interval (CI) limits for a ratio of the geometric mean of logarithmic transformed $AUC_{0-\infty}$, $AUC_{0-t}$, and $C_{max}$ for the two products or two methods are about 0.80 to about 1.25.

To show bioequivalence between two compounds or administration conditions pursuant to Europe's EMEA guidelines, the 90% CI limits for a ratio of the geometric mean of logarithmic transformed $AUC_{0-\infty}$ and $AUC_{0-t}$ for the two products or methods are about 0.80 to about 1.25. The 90% CI limits for a ratio of the geometric mean of logarithmic transformed $C_{max}$ for the two products or methods can have a wider acceptance range when justified by safety and efficacy considerations. For example the acceptance range can be about 0.70 to about 1.43, specifically about 0.75 to about 1.33, and more specifically about 0.80 to about 1.25.

In an embodiment, in given experiment, a controlled-release composition described herein is considered to be bioequivalent to the brand drug if both the Test/Reference ratio for the geometric mean of logarithmic transformed $AUC_{0-\infty}$, $AUC_{0-t}$, or $C_{max}$ ratio along with its corresponding lower and upper 90% CI limits are within a lower limit from about 0.80 and an upper limit from about 1.25. Thus, for direct comparison between the controlled-release composition and the brand drug, it is sometimes preferred to determine the pharmacokinetic parameters for the controlled-release composition and the brand drug side-by side in the same pharmacokinetic study.

In some embodiments a single dose pharmacokinetic study is performed under non-fasted or fasted conditions.

In other embodiments, the single dose pharmacokinetic study is conducted between the controlled-release composition and the reference listed drug using the strength specified by the FDA in APPROVED DRUG PRODUCTS WITH THERAPEUTIC EQUIVALENCE EVALUATIONS (ORANGE BOOK).

In some embodiments, in vivo pharmacokinetic studies are performed to compare all strengths of a particular active agent controlled-release composition with corresponding strengths of the brand drug. In other embodiments, an in vivo pharmacokinetic study is performed only for a particular strength of the active agent controlled-release composition of the present invention which is an equivalent strength to the reference listed drug product for the brand.

A dissolution profile is a plot of the cumulative amount of active agent released as a function of time. A dissolution profile can be measured utilizing the Drug Release Test <724>, which incorporates standard test USP 28 (Test <711>). A profile is characterized by the test conditions selected such as, for example, apparatus type, shaft speed, temperature, volume, and pH of the dissolution medium. More than one dissolution profile may be measured. For example, a first dissolution profile can be measured at a pH level approximating that of the stomach, and a second dissolution profile can be measured at a pH level approximating that of one point in the intestine or several pH levels approximating multiple points in the intestine.

The controlled-release compositions may be characterized by dissolution properties. In one embodiment, the controlled-release compositions as described herein may exhibit an in vitro dissolution profile substantially corresponding to the pattern for a brand drug or reference listed drug when tested in a particular dissolution medium. Exemplary dissolution media include purified water, acidic buffer of pH 4.5, 0.1 N HCl, 0.1N NaOH, 7.5 pH buffer, pH 6.8 phosphate buffer, 0.5M sodium dodecyl sulfate, and the like.

The controlled-release compositions, including a controlled-release composition comprising an active agent that has a solubility of greater than or equal to about 2.0 mg/ml of water at 25° C., exhibits a dissolution profile after combining the composition with 900 ml of pH 6.8 buffer at 37° C.±0.5° C. according to USP 28 <711> test method 1 (basket) at a speed of 100 rpm, wherein about 0 to about 20 wt %, specifically about 1 to about 18 wt %, and more specifically about 3 to about 13 wt % of the total amount of the active agent is released at 4 hours.

The controlled-release compositions, including a controlled-release composition comprising an active agent that has a solubility of greater than or equal to about 2.0 mg/ml of water at 25° C., exhibits a dissolution profile after combining the composition with 900 ml of pH 6.8 buffer at 37° C.±0.5° C. according to USP 28 <711> test method 1 (basket) at a speed of 100 rpm, wherein about 1 to about 25 wt %, specifically about 5 to about 20 wt %, and more specifically about 10 to about 15 wt % of the total amount of the active agent is released at 6 hours.

The controlled-release compositions, including a controlled-release composition comprising an active agent that has a solubility of greater than or equal to about 2.0 mg/ml of water at 25° C., exhibits a dissolution profile after combining the composition with 900 ml of pH 6.8 buffer at 37° C.±0.5° C. according to USP 28 <711> test method 1 (basket) at a speed of 100 rpm, wherein about 15 to about 30 wt %, specifically about 10 to about 25 wt %, and more specifically about 3 to about 20 wt % of the total amount of the active agent is released at 8 hours.

The controlled-release compositions, including a controlled-release composition comprising an active agent that has a solubility of greater than or equal to about 2.0 mg/ml of water at 25° C., exhibits a dissolution profile after combining the composition with 900 ml of pH 6.8 buffer at 37° C.±0.5° C. according to USP 28 <711> test method 1 (paddle) at a speed of 100 rpm, wherein about 5 to about 40 wt %, specifically about 10 to about 30 wt %, and more specifically about 15 to about 25 wt % of the total amount of the active agent is released at 10 hours.

The controlled-release compositions, including a controlled-release composition comprising an active agent that has a solubility of greater than or equal to about 2.0 mg/ml of water at 25° C., exhibits a dissolution profile after combining the composition with 900 ml of pH 6.8 buffer at 37° C.±0.5°

C. according to USP 28 <711> test method 1 (paddle) at a speed of 100 rpm, wherein about 5 to about 45 wt %, specifically about 10 to about 40 wt %, and more specifically about 5 to about 30 wt % of the total amount of the active agent is released at 12 hours.

The controlled-release compositions, including a controlled-release composition comprising an active agent that has a solubility of greater than or equal to about 2.0 mg/ml of water at 25° C., exhibits a dissolution profile after combining the composition with 900 ml of pH 6.8 buffer at 37° C.±0.5° C. according to USP 28 <711> test method 1 (paddle) at a speed of 100 rpm, wherein about 10 to about 55 wt %, specifically about 15 to about 45 wt %, and more specifically about 20 to about 30 wt % of the total amount of the active agent is released at 14 hours.

The controlled-release compositions, including a controlled-release composition comprising an active agent that has a solubility of greater than or equal to about 2.0 mg/ml of water at 25° C., exhibits a dissolution profile after combining the composition with 900 ml of pH 6.8 buffer at 37° C.±0.5° C. according to USP 28 <711> test method 1 (paddle) at a speed of 100 rpm, wherein about 10 to about 65 wt %, specifically about 15 to about 50 wt %, and more specifically about 20 to about 40 wt % of the total amount of the active agent is released at 18 hours.

EXAMPLES

The following examples further illustrate the invention but, of course, should not be construed as in any way limiting its scope.

Example 1

Controlled-Release Solid Dosage Forms (with Eudragit) Comprising Sodium Citrate and Quetiapine Fumarate Six controlled-release formulations (A, B, C, D, E and F) containing an ionic non-gelling matrix and sodium citrate (pH modifier) were prepared. These formulations contain quetiapine fumarate as the active agent. Three additional formulations (G, H, and I) were prepared with an ionic non-gelling matrix and no pH modifier. A comparative example containing a gelling matrix material (CE-A) was also prepared. The components and amounts of each formulation are provided in Table 1 below.

TABLE 1

| Ingredients | A | B | C | CE-A | D | E | F | G | H | I |
|---|---|---|---|---|---|---|---|---|---|---|
| Wet granulation components | | | | | | | | | | |
| Quetiapine Fumarate | 461.51 | 461.51 | 461.51 | 461.51 | 461.51 | 461.51 | 461.51 | 461.51 | 461.51 | 461.51 |
| Lactose Monohydrate, NF (Fast flo) | 77-81 | 77-81 | 77-81 | 39.76 | 77-81 | 77-81 | 77-81 | 77-81 | 77-81 | 77-81 |
| Eudragit L-100 | — | — | 77-83 | — | — | — | 77-83 | — | — | 77-83 |
| Eudragit S-100 | — | 77-83 | — | — | — | 77-83 | — | — | 77-83 | — |
| Eudragit L100 55 | 77-83 | — | — | — | 77-83 | — | — | 77-83 | — | — |
| Sodium Citrate Dihydrate | 82-86 (~10 wt %) | 82-86 (~10 wt %) | 82-86 (~10 wt %) | 84.00 | 38-42 (~5 wt %) | 38-42 (~5 wt %) | 38-42 (~5 wt %) | — | — | — |
| Microcrystalline Cellulose, NF (Avicel ® pH 101) | 38-42 | 38-42 | 38-42 | 39.76 | 81-87 | 81-87 | 81-87 | 79-85 | 79-85 | 79-85 |
| Hypromellose (Methocel ® E4M CR) | — | — | — | 40.00 | — | — | — | — | — | — |
| Hypromellose (Methocel ® E50LV) | — | — | * | 120.00 | — | — | — | — | — | — |
| Purified water | — | — | — | ** | — | — | — | — | — | — |
| Isopropyl Alcohol, USP | * | * | * | — | * | * | * | * | * | * |
| Extragranular components | | | | | | | | | | |
| Microcrystalline Cellulose, NF (Avicel PH 101) | 38-42 | 38-42 | 38-42 | — | 38-42 | 38-42 | 38-42 | 79-85 | 79-85 | 79-85 |
| Colloidal silicon Dioxide, NE (Cab-o-sil) | 3-5 | 3-5 | 3-5 | — | 3-5 | 3-5 | 3-5 | 3-5 | 3-5 | 3-5 |
| Magnesium Stearate, NF | 10-14 | 10-14 | 10-14 | 16.00 | 10-14 | 10-14 | 10-14 | 10-14 | 10-14 | 10-14 |
| Total | 801 | 801 | 801 | 801.03 | 801 | 801 | 801 | 801 | 801 | 801 |

\* IPA is used in manufacturing but does not appear in the final product
\*\* Purified water is used in manufacturing but does not appear in the final product Formulations A, B, C, D, E, F, G, H, and I were individually prepared by wet granulating wherein the wet granulation components include isopropyl alcohol. The resulting granulates were dried at 50° C. in an oven until LOD NLT 2%. The dried granulates were milled through a fitzmill using a 20 mesh screen with medium speed. The remaining microcrystalline cellulose and colloidal silicon dioxide were blended with the dried granulates; magnesium stearate was then added and blended. The final blend for Formulation A was compressed into tablets using 0.3125×0.75 modified capsule shape tooling. The final blend for Formulations B and C were compressed into tablets on beta press using 0.36 "X 0.74" modified capsule tooling. Target hardness=25 kp, low hardness=20 kp and high hardness=30 kp.

Formulation CE-A was prepared by wet granulating wherein the wet granulation components include purified water. The resulting granulates were dried at 50° C. in an oven until LOD NLT 2%. The dried granulates were milled through a fitzmill using a 20 mesh screen with medium speed. The magnesium stearate was blended with the dried granulates and blended. The final blend for Formulation CE-A was compressed into tablets using 0.3125×0.75 modified capsule shape tooling.

Tablets prepared from Formulations A, B, C, D, E, F, G, H, and I and Comparative Example CE-A were tested in 900 ml of pH 6.8 phosphate buffer as the dissolution medium at a temperature of 37° C.±2° C. under conditions of USP apparatus 1, basket at a speed of 100 rpm. The resulting release profiles are provided in Table 2 below as percent released. Tablets prepared from Formula B eroded faster than those prepared from Formulas A and C and the dissolution rate was faster. This is likely inherent in the bonding characteristics of the polymer. Formulas A and C contain Eudragit L-100 55 and L-100 respectively. Tablets from these products did not erode. These ionic non-gelling matrix polymers are soluble at pHs above 5.5 and 6, respectively. Formula A with the ionic non-gelling matrix polymer having a lower pH (5.5) solubility showed a faster release than Formula C with the polymer having a higher pH (6.0). The release rate can be modified faster or slower in each case by increasing or decreasing the ionic non-gelling matrix polymer content.

Also shown by the dissolution data, the release rates from the formulations having amounts of the pH modifier sodium citrate (formulations A, B, C, D, E, and F) were slower than corresponding formulations with no pH modifier (formulations G, H, and I).

TABLE 2

| Time (hours) | A | B | C | CE-A | D | E | F | G | H | I |
|---|---|---|---|---|---|---|---|---|---|---|
| 0 | 0 | 6 | 0 | 0 | 0 | 0 | 6 | 0 | 0 | 0 |
| 1 | 3 | 4 | 3 | 7 | 4 | 3 | 3 | 5 | 10 | 5 |
| 2 | 6 | 6 | 5 | 12 | 7 | 5 | 5 | 10 | 23 | 10 |
| 3 | 9 | 8 | 7 | 17 | 10 | 9 | 7 | 15 | 33 | 13 |
| 4 | 11 | 13 | 8 | 22 | 12 | 17 | 8 | 20 | 42 | 16 |
| 6 | 18 | 32 | 12 | 30 | 18 | 47 | 13 | 28 | 55 | 22 |
| 8 | 24 | 47 | 15 | 38 | 23 | 68 | 18 | 36 | 64 | 28 |
| 10 | 30 | 54 | 18 | 46 | 28 | 79 | 23 | 43 | 70 | 33 |
| 12 | 35 | 59 | 23 | 53 | 32 | 86 | 31 | 49 | 75 | 38 |
| 14 | 38 | 63 | 29 | 60 | 36 | 91 | 40 | 55 | 77 | 42 |
| 18 | 48 | 68 | 37 | 73 | 43 | 96 | 48 | 64 | 81 | 50 |

The terms "a" and "an" do not denote a limitation of quantity, but rather denote the presence of at least one of the referenced item. The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A controlled-release composition, comprising:
 a non-gelling matrix consisting of
  a pharmaceutically effective amount of an active agent or a pharmaceutically acceptable salt, solvate, ester, and/or prodrug thereof,
  an ionic non-gelling matrix polymer that is practically insoluble and unswellable at a first aqueous fluid pH and is soluble at a second aqueous fluid pH,
  a pH modifier which is present in an amount from about 2 to about 50 wt % based on the total weight of the composition; and
  a soluble, non-gelling pharmaceutically acceptable excipient; and
 the composition is substantially free of a gelling or swelling excipient and does not contain a functional coating.

2. The controlled-release composition of claim 1, wherein the ionic non-gelling matrix polymer is selected from the group consisting of cellulose acetate phthalate, cellulose acetate succinate, hypromellose phthalate, hypromellose acetate succinate, a methacrylic acid-methyl methacrylate co-polymer, polyvinylacetate phthalate, hydroxyethyl cellulose phthalate, cellulose acetate maleate, cellulose acetate trimellitate, cellulose acetate butyrate, cellulose acetate propionate, a methacrylic acid-methyl methacrylate co-polymer, a methacrylic acid-ethyl acrylate co-polymer, a methacrylic acid-methyl acrylate-methyl methacrylate, and a combination thereof.

3. The controlled-release composition of claim 1, wherein the ionic non-gelling matrix polymer is selected from the group consisting of a methacrylic acid-methyl methacrylate co-polymer, a methacrylic acid-ethyl acrylate co-polymer, methacrylic acid-methyl acrylate-methyl methacrylate, and a combination thereof.

4. The controlled-release composition of claim 1, wherein the ionic non-gelling matrix polymer is present in an amount from about 5 to about 85 wt % based on the total weight of the composition.

5. The controlled-release composition of claim 1, wherein the active agent is selected from the group consisting of an antihypertensive agent, an antidepressant agent, an antianxiety agent, an anticlotting agent, an anticonvulsant agent, a blood glucose-lowering agent, a decongestant agent, an antihistamine agent, an antitussive agent, an anti-inflammatory agent, an antipsychotic agent, a cognitive enhancer, a cholesterol-reducing agent, an antiobesity agent, an autoimmune disorder agent, an anti-impotence agent, an antibacterial agent, an antifungal agent, a hypnotic agent, an anti-Parkinsonism agent, an antiviral agent, an anti-neoplastic agent, a barbituate agent, a sedative agent, a nutritional agent, a beta blocker, an emetic agent, an anti-emetic agent, a diuretic agent, an anticoagulant agent, a cardiotonic agent, an androgen agent, a corticoid, an anabolic agent, a growth hormone secretagogue, an anti-infective agent, a coronary vasodilator, a carbonic anhydrase inhibitor, an antiprotozoal agent, a gastrointestinal agent, a serotonin antagonist, an anesthetic agent, a hypoglycemic agent, a dopaminergic agent, an anti-Alzheimer's Disease agent, an anti-ulcer agent, a platelet inhibitor, a glycogen phosphorylase inhibitor, a muscle relaxant, and a pharmaceutically acceptable combination thereof.

6. The controlled-release composition of claim 5, wherein the active agent has a solubility of greater than or equal to about 2.0 mg/ml in an aqueous medium at room temperature.

7. The controlled-release composition of claim 5, wherein the active agent is quetiapine, or a salt, solvate, ester, and/or prodrug thereof.

8. The controlled-release composition of claim 1, wherein the pH modifier is a pharmaceutically acceptable organic acid, or an alkali metal or alkaline earth metal salt thereof.

9. The controlled-release composition of claim 7, wherein the pH modifier is sodium citrate.

10. The controlled-release composition of claim 1, wherein the soluble, non-gelling pharmaceutically acceptable excipient is a sugar polyol, a monosaccharide, a disaccharide, a polysaccharide, or a combination thereof.

11. The controlled-release composition of claim 1, wherein the soluble, non-gelling pharmaceutically acceptable excipient is lactose, sucrose, dextrose, fructose, glucose, maltose, polydexotrose, sorbitol, xylitol, mannitol, galactitol, maltitol, lactitol, erythritol, maltose, dextrin, maltodextrin, xylose, galactose, trehalose, tagatose, or a combination thereof.

12. The controlled-release composition of claim 1, wherein the soluble, non-gelling pharmaceutically acceptable excipient is present in an amount from about 1 to about 70 wt % based on the total weight of the composition.

13. The controlled-release composition of claim 1, wherein the first aqueous fluid has a pH equal to or less than about 4.5, and the second aqueous fluid has a pH greater than about 4.5.

14. The controlled-release composition of claim 12, wherein the first aqueous fluid is human gastric fluid, and the second aqueous fluid is human intestinal fluid.

15. The controlled-release composition of claim 1, wherein the composition is a tablet, a capsule, a granule, a mini-tablet, or a pellet.

16. The controlled-release composition of claim 1, wherein the controlled-release composition is in a once a day dosage form or a twice a day dosage form.

17. The controlled-release composition of claim 1, wherein the composition exhibits a dissolution profile after combining the composition with 900 ml of pH 6.8 buffer at 37° C.±0.5° C. according to USP 28 <711> test method 1 (basket) at a speed of 100 rpm, wherein from about 1 to about 30 wt % of the total amount of the active agent is released at 3 hours.

18. The controlled-release composition of claim 1, wherein the composition exhibits a dissolution profile after combining the composition with 900 ml of pH 6.8 buffer at 37° C.±0.5° C. according to USP 28 <711> test method 1 (basket) at a speed of 100 rpm, wherein from about 1 to about 40 wt % of the total amount of the active agent is released at 4 hours.

19. The controlled-release composition of claim 1 wherein the composition exhibits a dissolution profile after combining the composition with 900 ml of pH 6.8 buffer at 37° C.±0.5° C. according to USP 28 <711> test method 1 (paddle) at a speed of 100 rpm, wherein from about 1 to about 45 wt % of the total amount of the active agent is released at 6 hours.

20. The controlled-release composition of claim 1 wherein the composition exhibits a dissolution profile after combining the composition with 900 ml of pH 6.8 buffer at 37° C.±0.5° C. according to USP 28 <711> test method 1 (paddle) at a speed of 100 rpm, wherein from about 15 to about 70 wt % of the total amount of the active agent is released at 8 hours.

21. The controlled-release composition of claim 1 wherein the composition exhibits a dissolution profile after combining the composition with 900 ml of pH 6.8 buffer at 37° C.±0.5° C. according to USP 28 <711> test method 1 (paddle) at a speed of 100 rpm, wherein from about 18 to about 80 wt % of the total amount of the active agent is released at 10 hours.

22. The controlled-release composition of claim 1 wherein the composition exhibits a dissolution profile after combining the composition with 900 ml of pH 6.8 buffer at 37° C.±0.5° C. according to USP 28 <711> test method 1 (paddle) at a speed of 100 rpm, wherein from about 25 to about 85 wt % of the total amount of the active agent is released at 12 hours.

23. The controlled-release composition of claim 1 wherein the composition exhibits a dissolution profile after combining the composition with 900 ml of pH 6.8 buffer at 37° C.±0.5° C. according to USP 28 <711> test method 1 (paddle) at a speed of 100 rpm, wherein from about 25 to about 90 wt % of the total amount of the active agent is released at 14 hours.

24. The controlled-release composition of claim 1 wherein the composition exhibits a dissolution profile after combining the composition with 900 ml of pH 6.8 buffer at 37° C.±0.5° C. according to USP 28 <711> test method 1 (paddle) at a speed of 100 rpm, wherein from about 25 to about 95 wt % of the total amount of the active agent is released at 18 hours.

25. The controlled-release composition of claim 1, wherein a dissolution profile of the composition is substantially the same as a dissolution profile of an equivalent strength of a reference drug product when the dissolution profile is determined by using the conditions according to USP 28 <711> test method 2 (paddle), using of 900 ml of a dissolution medium at 37° C.±0.5° C., and 50 rpm paddle speed, wherein the dissolution medium is purified water, 0.1N HCl, 0.1N NaOH, 7.5 pH buffer, 6.8 pH buffer, or 0.5M sodium dodecyl sulfate.

26. The controlled-release composition of claim 1, wherein the composition is bioequivalent to an equivalent strength of a reference drug product.

27. The controlled-release composition of claim 26, wherein the 90% confidence limits of a ratio of a geometric mean of logarithmic transformed $AUC_{0-\infty}$ of the composition to a geometric mean of logarithmic transformed $AUC_{0-\infty}$ of the reference drug is about 0.80 to about 1.25.

28. The controlled-release composition of claim 26, wherein the 90% confidence limits of a ratio of a geometric mean of logarithmic transformed $AUC_{0-t}$ of the composition to a geometric mean of logarithmic transformed $AUC_{0-t}$ of the reference drug is about 0.80 to about 1.25.

29. The controlled-release composition of claim 26, wherein the 90% confidence limits of a ratio of a geometric mean of logarithmic transformed $C_{max}$ of the composition to a geometric mean of logarithmic transformed $C_{max}$ of the reference drug is about 0.7 to about 1.43.

30. The controlled-release composition of claim 26, wherein the 90% confidence limits of a ratio of a geometric mean of logarithmic transformed $C_{max}$ of the composition to a geometric mean of logarithmic transformed $C_{max}$ of the reference drug is about 0.8 to about 1.25.

31. A method of treating a patient in need of an active agent therapy, comprising administering the controlled-release composition of claim 1 to the patient.

\* \* \* \* \*

UNITED STATES PATENT AND TRADEMARK OFFICE
CERTIFICATE OF CORRECTION

| | | |
|---|---|---|
| PATENT NO. | : 8,632,805 B2 | Page 1 of 1 |
| APPLICATION NO. | : 12/143460 | |
| DATED | : January 21, 2014 | |
| INVENTOR(S) | : Naringrekar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 636 days.

Signed and Sealed this
Twenty-first Day of April, 2015

Michelle K. Lee
*Director of the United States Patent and Trademark Office*